United States Patent [19]

Okazaki et al.

[11] 4,091,208

[45] May 23, 1978

[54] α-(9-ANTHRYL)-β-(3-CARBAZOLYL)ETHYLENE DERIVATIVES

[75] Inventors: Mitsuo Okazaki, Tama; Akihiro Yamaguchi, Asaka; Masaomi Sasaki, Kawasaki, all of Japan

[73] Assignee: Ricoh Co., Ltd., Tokyo, Japan

[21] Appl. No.: 785,569

[22] Filed: Apr. 7, 1977

[30] Foreign Application Priority Data

Apr. 19, 1976  Japan ................................. 51-44735

[51] Int. Cl.² ..................... G03C 1/16; C07D 209/82
[52] U.S. Cl. ..................................... 542/454; 96/88; 542/465
[58] Field of Search ............................... 542/454, 465

[56] References Cited

U.S. PATENT DOCUMENTS

| 3,796,707 | 3/1974 | Siegrist et al. ...................... 542/454 |
| 3,932,301 | 1/1976 | Crounse et al. ................. 542/454 X |

FOREIGN PATENT DOCUMENTS 684,139  12/1952  United Kingdom ................. 542/433

Primary Examiner—Winston A. Douglas
Assistant Examiner—Thomas A. Waltz
Attorney, Agent, or Firm—Blanchard, Flynn, Thiel, Boutell & Tanis

[57] ABSTRACT

α-(9-Anthryl)-β-(3-carbazolyl)ethylene derivatives, process for preparing same and electrophotographic light-sensitive materials containing α-(9-anthryl)-β-(3-carbazolyl)ethylene derivative.

2 Claims, 1 Drawing Figure

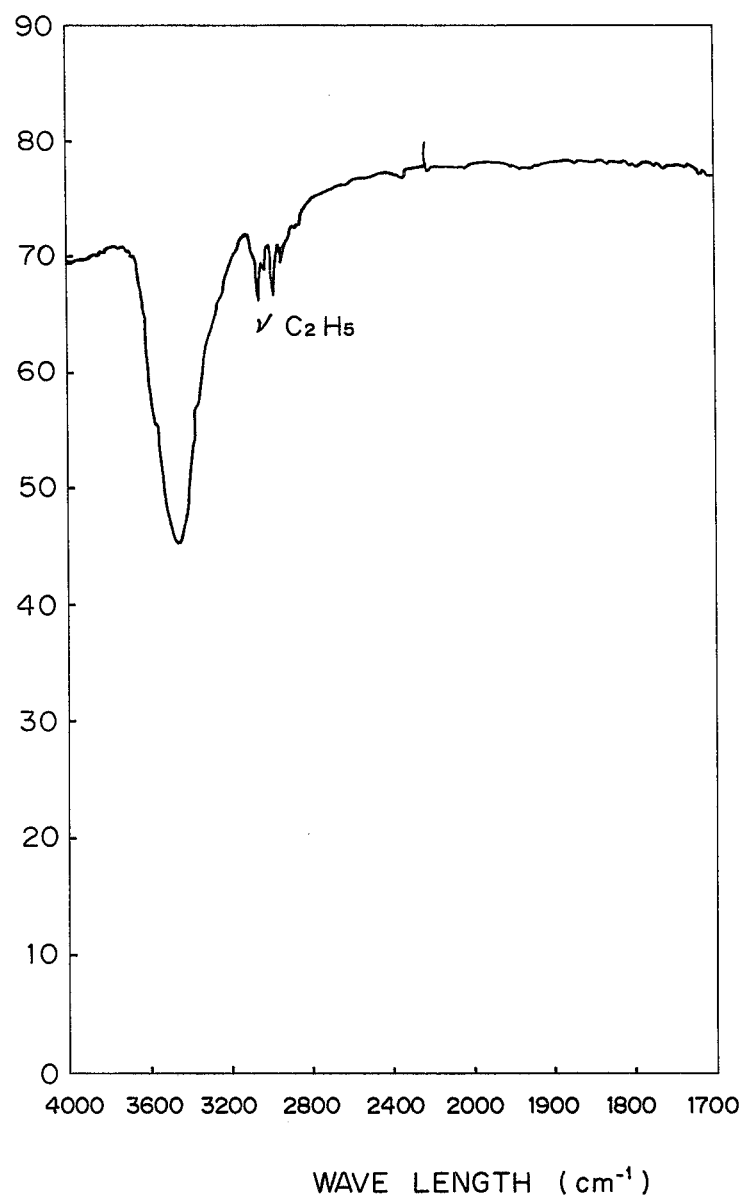

α-(9-ANTHRYL)-β-(3-CARBAZOLYL)ETHYLENE DERIVATIVES

DESCRIPTION OF THE INVENTION:

The present invention relates to α-(9-anthryl)-β-(3-carbazolyl) ethylene derivatives, process for preparing same and electrophotographic light-sensitive materials containing α-(9-anthryl-β-(3-carbazolyl)ethylene derivative.

α-(9-anthryl)-β-(3-carbazolyl)ethylene derivatives are organic compounds having the following general formula (I):

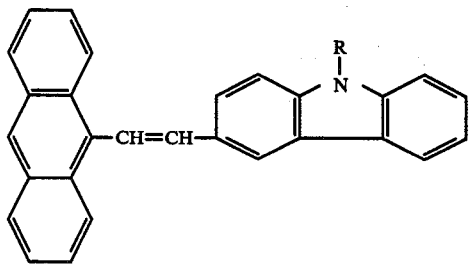
(I)

wherein R is a lower alkyl group of from 1 to 4 carbon atoms.

Among α-(9-anthryl)-β-(3-carbazolyl)ethylene derivatives, α-(9-anthryl)-β-[3-(N-ethylcarbazolyl)]ethylene having the following formula (II), in which R is $C_2H_5$) is the most useful compound:

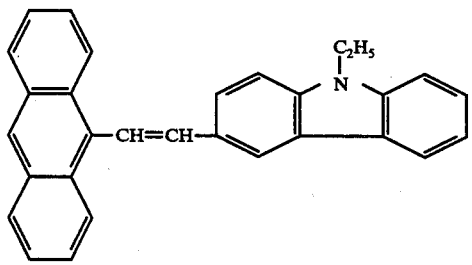
(II)

Electrophotographic light-sensitive materials of the present invention can be prepared by forming a photoconductive layer on a support, said photoconductive layer comprising α-(9-anthryl)-β-(3-carbazolyl)ethylene derivatives, especially α-(9-anthryl)-β-[3-N-ethylcarbazolyl)]ethylene.

α-(9-anthryl)-β-(3-carbazolyl)ethylene derivatives having the general formula (I) can be obtained by reacting to a compound of the following formula (III) with a compound of the following formula (IV) in the presence of an alkaline catalyst in an organic solvent:

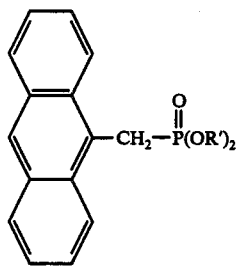
(III)

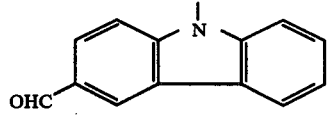
(IV)

wherein R' and R" are a lower alkyl group of from 1 to 4 carbon atoms.

α-(9-anthryl)-β-[3-(N-ethylcarbazolyl)]ethylene of the formula (II) can be obtained by mixing diethyl 9-anthrylmethylphosphonate of the following formula (V) and N-ethylcarbazole-3-aldehyde of the following formula (VI) at room temperature to 100° C in the presence of an alkaline catalyst in an organic solvent:

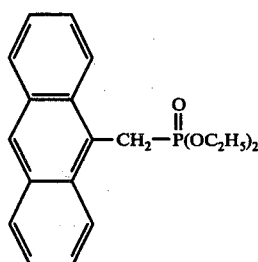
(V)

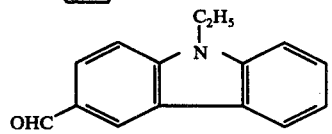
(VI)

Preferred alkaline catalysts include sodium hydroxide, potassium hydroxide, alkoxide of sodium or patassium, sodium hydride, potassium hydride, sodium amide and potassium amide.

Preferred organic solvents include alcohols such as methyl alcohol, ethyl alcohol, iso-propyl alcohol and tertbutyl alcohol, benzene and its derivatives such as toluene, xylene, and chlorobenzene, dioxane, N,N-dimethylformamide, dimethyl sulfoxide, and tetrahydrofuran.

Dialkyl 9-anthrylmethylphosphonate of the formula (III) can be obtained by heating a mixture of trialkyl phosphite and 9-halomethylanthracene such as 9-chloromethylanthracene in toluene or without organic solvent. The trialkyl phosphite may be trimethyl phosphite or triethyl phosphite.

α-(9-anthryl)-β-(3-carbazolyl)ethylene derivatives of the general formula (I) have excellent photoconductive property, so they are used as photoconductive substance for forming a photoconductive layer of electrophotographic light-sensitive materials. In the photoconductive layer comprising such derivatives, optical or chemical sensitizers such as dyes or electron acceptors may be contained. Preferred sensitizers include Methyl Violet, Crystal Violet, Methylene Blue and 2,4,7-trinitro-9-fluorenone.

Electrophotographic light-sensitive materials having high quality can be obtained by adding organic pigments or inorganic photoconductive substances to the photoconductive layer comprising α-(9-anthryl)-β-(3-carbazolyl)ethylene derivatives. Said organic pigments are, for example, metal free phthalocyanine, copper phthalocyanine, Diane Blue (C.I. No. 21180), Indanthrene Red Violet RRN (C.I. No. 73395), indigo, thioindigo, Indanthrene Scarlet R (C.I. No. 71140), and said inorganic photoconductive substances are, for example, zinc oxide, cadmium sulfide and selenium.

Said electrophotographic light-sensitive materials comprising organic pigments or inorganic photoconductive substances and α-(9-anthryl)-β-(3-carbazolyl)ethylene derivatives will be explained as follows:

In the recent years, novel electrophotographic light-sensitive materials comprise charge generating substances and charge transporting substances. For example, in U.S. Pat. Nos. 3,791,826 and 3,837,851, there have been disclosed electrophotographic light-sensitive materials comprising the charge generating substances such as inorganic photoconductive substances and the charge transporting substances such as 2,4,7-trinitro-9-fluorenone or tri-aryl pyrazoline compounds.

The charge generating substances include inorganic photoconductive substances such as Se, Se-Te alloy, Se-Te-As alloy, ZnO, CdS and cadmium sulfoselenide, and organic pigments such as cyanine dye, phthalocyanine, disazo, indigoid, quinacridone, polynuclear quinone, bis-benzimidazole, perylene, methine dye, azo dye, xanthene dye and violantrone.

On the contrary, useful charge transporting substances have not yet been found. α-(9-anthryl)-β-(3-carbazolyl)ethylene derivatives of the present invention are one of the useful charge transporting substances.

Electrophotographic light-sensitive materials comprising such charge transporting substance can be made by forming a photoconductive layer in thickness of 3 to 50μ on an electroconductive support, said photoconductive layer comprising a disperse system of 5 to 50% by weight of charge generating substance and 30 to 80% by weight of charge transporting substance in an insulating organic high molecular compound.

The electroconductive support may be a metallic plate such as a plate of aluminum and stainless steel, or a metalevaporated plastic film. The insulating organic high molecular compound may be polyamide, polyurethane, polyester, epoxy resin, alkyd resin, acrylic resin, silicone resin and cellulose.

Alternatively, the photoconductive layer may be formed in two layers by forming a layer of charge generating substance in thickness of 1 to 5μ on an electronconductive support and then forming a layer of charge transporting substance in thickness of 3 to 50μ on the layer of charge generating substance.

The formation of the photoconductive layer can be effected by coating a dispersion liquid of charge generating substance and/or charge transporting substance in an organic solvent such as toluene or tetrahydrofuran on a support and then drying it.

BRIEF DESCRIPTION OF THE DRAWING

The drawing is the infrared absorption spectrum of α-(9-anthryl)-β-[3-(N-ethylcarbazolyl)]ethylene prepared in Example 1.

DESCRIPTION OF THE PREFERRED EMBODIMENTS

The following examples are given by way of illustration only.

EXAMPLE 1.

After a mixture of 28.5g of 9-chloromethylanthracene and 62.3g of triethyl phosphite was heated at a temperature of 140° C for 2 hours with stirring, the mixture was cooled to a room temperature to obtain light yellowish needle-like crystalline product. The crystalline product was filtered off and washed with petroleum ether, and then dried. A crude product was obtained in a yield of 34.4g (83.8%). A pure crystalline product of diethyl 9-anthrylmethylphosphonate (m.p. 103.5° C – 104° C) was obtained by the recrystallization of the crude product from n-hexane in a yield of 31.2g.

| Analysis: | C(%) | H(%) |
|---|---|---|
| Calculated for $C_{19}H_{21}O_3P$ | 69.50 | 6.45 |
| Found | 69.51 | 6.43 |

1.7g of diethyl 9-anthrylmethylphosphonate obtained above, 1.1g of potassium-t-butoxide and 1.5ml of N,N-dimethylformamide were mixed, and to the mixture was added 1.2g of N-ethylcarbazole-3-aldehyde. After the mixture was stirred at room temperature for 5 hours, 10ml of water was added to the mixture to obtain a yellowish crystalline product. The crystalline product was filtered off and washed with water, and then dried. A crude product (m.p. 206° C – 208° C) was obtained in a yield of 1.9g (95.0%). A pure crystalline product of α-(9-anthryl)-β-[3-(N-ethylcarbazolyl)]ethylene (m.p. 208° C – 209° C) was obtained by the recrystallization of the crude product from cyclohexane in a yield of 1.7g.

| Analysis: | C(%) | H(%) | N(%) |
|---|---|---|---|
| Calculated for $C_{30}H_{23}N$ | 90.64 | 5.83 | 3.52 |
| Found | 90.53 | 5.84 | 3.52 |

Infrared absorption spectrum (KBr tablet method) $\nu C_2H_5\ 3100 - 2900 cm^{-1}$ as shown in the accompanying drawing.

EXAMPLE 2

A light-sensitive dispersion liquid containing a photoconductive composition for use in the production of a photoconductive layer was prepared by mixing the following ingredients in a ball mill of stainless steel:

α-(9-anthryl)-62 -]3-(N-ethylcarbazolyl)]ethylene (Formula II)     10 g
    0.1 g $H_3CO-\bigcirc-\underset{\bigcirc}{\overset{\bigcirc-OCH_3}{\underset{O^+}{\bigcirc}}}-\bigcirc-OCH_3 \cdot ClO_4^-$ polymethyl acrylate     5g
toluene     100 g This light-sensitive dispersion liquid was applied as a coat on tracing paper, using a wire bar, and then dried to obtain an electrophotographic light-sensitive material having a photoconductive layer of about 12μ in thickness formed on the tracing paper.

After the photoconductive layer of the material obtained above was negatively charged by a corona discharge of about −6kV, and then imagewise exposed to a tungsten filament lamp of 20 lux, the material was developed by using a developing liquid (sold by Ricoh Co. under the trade name of BS-1) to obtain a copy having a vivid image. This copy can be used as an intermediate original.

EXAMPLE 3

2% dispersion liquid of Diane Blue (C.I. No. 21180) in tetrahydrofuran was crushed in a ball mill of stainless steel to obtain a dispersion liquid containing Diane Blue of 1μ in particle size. 750mg of the dispersion liquid obtained above, 1.5g of 10% solution of Polyester Adhesive 49000 (Trademark of polyester resin sold by E.I. Du Pont de Nemours & Co., Inc.) in tetrahydrofuran and 150mg of α-(9-anthryl)-β-[3-(N-ethylcarbazolyl)-]ethylene were mixed in a ball mill to prepare a light-sensitive dispersion liquid for use in the production of a photoconductive layer.

The light-sensitive dispersion liquid was applied as a coat on an aluminum plate, using a doctor blade, and then dried to obtain an electrophotographic light-sensitive material having a photoconductive layer of about 19μ in thickness formed on the aluminum plate.

The sensitivity of the material obtained above was evaluated as follows:

The photoconductive layer of the material was positively charged by a corona discharge of about +6kV to obtain a surface electric potential. This surface electric potential was +810V. The charged material was exposed to a tungsten filament lamp whose illuminance at the surface of the light-sensitive layer was adjusted to be 20 lux. The time (seconds) required to reduce the surface electric potential to one half of the initial surface potential was measured. The amount of exposure required to reduce the surface electric potential to one half($E_{1/2}$) are calculated by "20 lux X time (seconds)". This amount of exposure ($E_{1/2}$) was 4.1 lux sec.

EXAMPLE 4.

2% dispersion liquid of Diane Blue in tetrahydrofuran prepared in Example 3 was applied on an aluminum plate, using a doctor blade, and then dried to form a layer of 0.5μ in thickness. Onto this layer was applied, using a doctor blade, a light-sensitive solution prepared by dissolving 225mg of α-(9-anthryl)-β-[3-(N-ethylcarbazolyl)]ethylene in 2.25g of 10% solution of Polyester Adhesive 49000 in tetrahydrofuran prepared in Example 3, and then dried to obtain an electrophotographic light-sensitive material having a photoconductive layer of about 15μ in thickness.

The sensitivity of the material obtained above was evaluated in the manner as shown in EXAMPLE 3.

The photoconductive layer of the material was negatively charged by a corona discharge of about -6kV. The surface electric potential was -850V. The amount of exposure required to reduce the surface electric potential to one half($E_{1/2}$) was 5.2 lux-sec.

EXAMPLE 5.

An electrophotographic light-sensitive material was obtained by repeating the same procedure as that of Example 3 except that metal free phthalocyanine was used instead of Diane Blue.

The sensitivity of the material obtained above was evaluated in the same manner as that described in Example 1. The surface electric potential was +795V. The amount of exposure ($E_{1/2}$) was 3.8 lux sec.

We claim:

1. α-(9-anthryl)-β-(3-carbazolyl)ethylene derivative having the formula (I):

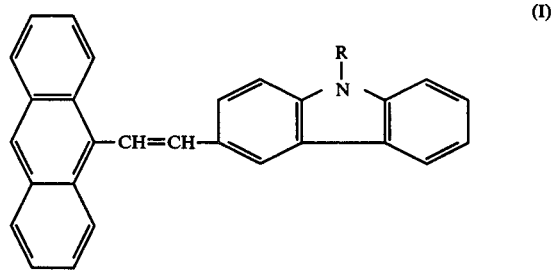

wherein R is a lower alkyl group of from 1 to 4 carbon atoms.

2. α-(9-anthryl)-β-(3-carbozolyl)ethylene derivative according to claim 1 wherein said derivative has the formula (II):

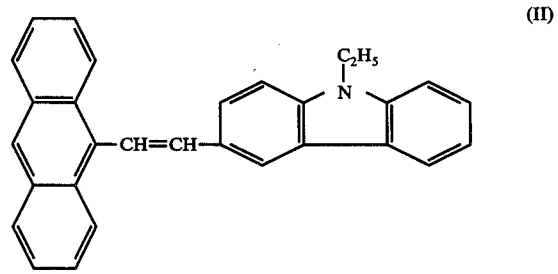

* * * * *